US00PP18223P2

(12) United States Plant Patent
Hayakawa

(10) Patent No.: US PP18,223 P2
(45) Date of Patent: Nov. 20, 2007

(54) ***CLEMATIS* PLANT 'FAIRY BLUE'**

(50) Latin Name: *Clematis viticella*
Varietal Denomination: Fairy Blue

(75) Inventor: Hiroshi Hayakawa, Izumi-cho (JP)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 10/367,447

(22) Filed: Feb. 14, 2003

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell

(57) ABSTRACT

A new *Clematis* cultivar which produces attractive violet flowers. This new and distinct variety has shown to be uniform and stable in the resulting generations from asexual propagation.

1 Drawing Sheet

Botanical designation: *Clematis viticella.*
Variety denomination: 'Fairy Blue'.

SUMMARY OF THE DISCOVERY

The present discovery constitutes a new and distinct variety of *Clematis* which was discovered in a cultivated area. The mutation resulted from a naturally occurring branch mutation of unknown causation on a *Clematis* plant growing in a cultivated area. The resulting mutation was evaluated and asexually propagated in a controlled environment. The new variety is named 'Fairy Blue'.

The *clematis* plant of the present discovery has a unique characteristic which distinguishes it from the original *clematis,* 'H.F. Young'. 'Fairy Blue' has an abundance of sterile petaloid stamens at the flower center.

'Fairy Blue' is a sport of the *clematis* variety 'H.F. Young', non-patented, selected by Hiroshi Hayakawa at the Anjo *Clematis* Garden in Aichi Prefecture, Japan, May 1994.

Asexual reproduction of 'Fairy Blue' by cuttings was first done by Raymond J. Evison in Domarie Vineries Les Sauvagees, St. Sampsons, Guernsey, Channel Islands, United Kingdom in 1994. This initial and subsequent propagations have demonstrated that the characteristics of 'Fairy Blue' are true to type and are transmitted from one generation to the next.

BRIEF DESCRIPTION OF THE DRAWING

The accompanying color illustration shows as true as is reasonably possible to obtain in color photographs of this type, the typical characteristics of the buds, flowers and leaves of the new variety, with different flowers shown in various stages of maturity. The flower form, flower colors, flower buds, floral parts, flower pedicels and the cultivar's foliage are depicted.

DETAILED DESCRIPTION OF THE VARIETY

The following is a detailed description of 'Fairy Blue', as observed in its growth throughout the flowering period in glasshouses at Domarie Vineries Les Sauvagees, St. Sampsons, Guernsey, Channel Islands, United Kingdom. Observed plants are 24 months of age, grown in 5 gallon pots. Certain phenotypical characteristics of the variety may vary under different environmental, cultural, agronomic, seasonal, and climatic conditions. Color references are made using The Royal Horticultural Society (London, England) Colour Chart, 1995, except where common terms of color are used. For a comparison, the nearest existing *Clematis* variety is Multi Blue. Chart 1 details the physical characteristics of 'Fairy Blue' and the comparison variety.

CHART 1

| | 'Fairy Blue' | Multi Blue |
|---|---|---|
| Flowering | Early, Compact | Late, Less compact |
| Tepal Color | Violet 87A | Violet 86A |
| Flower Center | Violet to white | Dark violet |

FLOWER AND FLOWER BUD

Blooming habit: First flowers appear in May. Second flowering in September.

Flower bud:
- *Size.*—35 mm in length. Diameter is 8 to 10 mm.
- *Bud form.*—Elliptical.
- *Bud color.*—Yellow-Green Group 142B at ¼ opening.
- *Tepals.*—Violet Group 87A.
- *Peduncle.*—Surface: Smooth. Length: 90-120 mm average length. Color: Medium green. Green Group 143C. Orientation: Horizontal.
- *Borne.*—Singly.

Flower bloom:
- *Size.*—Diameter is 120 mm. Depth is 20 to 30 mm.
- *Form.*—Flat. Completely open, outer tepals are flat.
- *Color.*—Upper surface is Violet Group 87A. Lower surface is Violet Group 87A to 87B with a central bar the color of White Group 155A.
- *Fragrance.*—None.
- *Lasting quality on plant.*—10 days on average.

Tepals:
- *Tepal count.*—8 on average.
- *Shape.*—Individual tepal shape is elliptical. Apex is mucronate. Base is acute.

*Size.*—On average, 60 mm long by 27 mm wide.
*Cross section.*—Slightly concave.
*Margins.*—Entire with weak undulations.
*Recurvature of tip.*—Slight.
*Persistence.*—Tepals drop off cleanly while inner ruff of petaloid stamens remains.

Reproductive organs: Sterile flowers are comprised of 50 to 100 petaloid stamens, 30 to 40 mm in length. Petaloid stamens are Violet Group 87D in color on young flowers, and Violet Group 84D to white on mature flowers. No seed is produced.

PLANT

Plant form: Climbing and spreading.
Plant growth: Moderately vigorous.
Height: When trellised, one seasons growth attains 2.0 meters.
Spread: Typically 100 cm.
Hardiness: Trials to date show the variety hardy in USDA zones 6-9.
Stems:
*Color.*—Young wood: Green Group 138A to Yellow-Green Group 144A. Older wood: Greyed Orange 166A.
*Internodes.*—Cylindrical in cross section. Length 100 cm.
*Dimensions.*—Stems are typically 100 cm from the base of the plant to the top flowering portion, and 3 to 4 mm in diameter.
*Petioles.*—Petiole: 40 to 50 mm. Petiolus: 30 to 60 mm. Petiolule: 0 to 10 mm. Color: Green Group 138A to Greyed Orange Group 166A. Clasping: Clasps by leaf petiolus.
*Bark.*—Young wood: Smooth with light pubescence. Older wood: Rough.

Plant foliage:
*Type.*—Deciduous, trifoliate.
*Leaf size.*—Compound leaves are generally 120 mm long by 120 mm wide. Terminal leaflets are normally 60 mm long by 35 mm wide.
*Abundance.*—Abundant.
*Color.*—Top: Green Group 137B. Bottom: Green Group 137C.
*Shape.*—Elliptical. Base is rounded, occasionally cordate. Apex is acute to cirrhose.
*Margins.*—Terminal leaflet margin is entire.
*Texture.*—Upper side: Glabrous. Lower side: Glabrous.
*Surface.*—Matte Finish.

Disease resistance: Subject to any disease which normally attacks the species. 'Fairy Blue' has been found to be more resistant to powdery mildew than other cultivars.

It is claimed:

1. A new and distinct variety of *Clematis* plant, named 'Fairy Blue', substantially as herein illustrated and described, as a distinct and novel *Clematis* variety due to its abundant violet flowers, excellent flower longevity, and compact growth making it suitable for nursery production in containers.

* * * * *

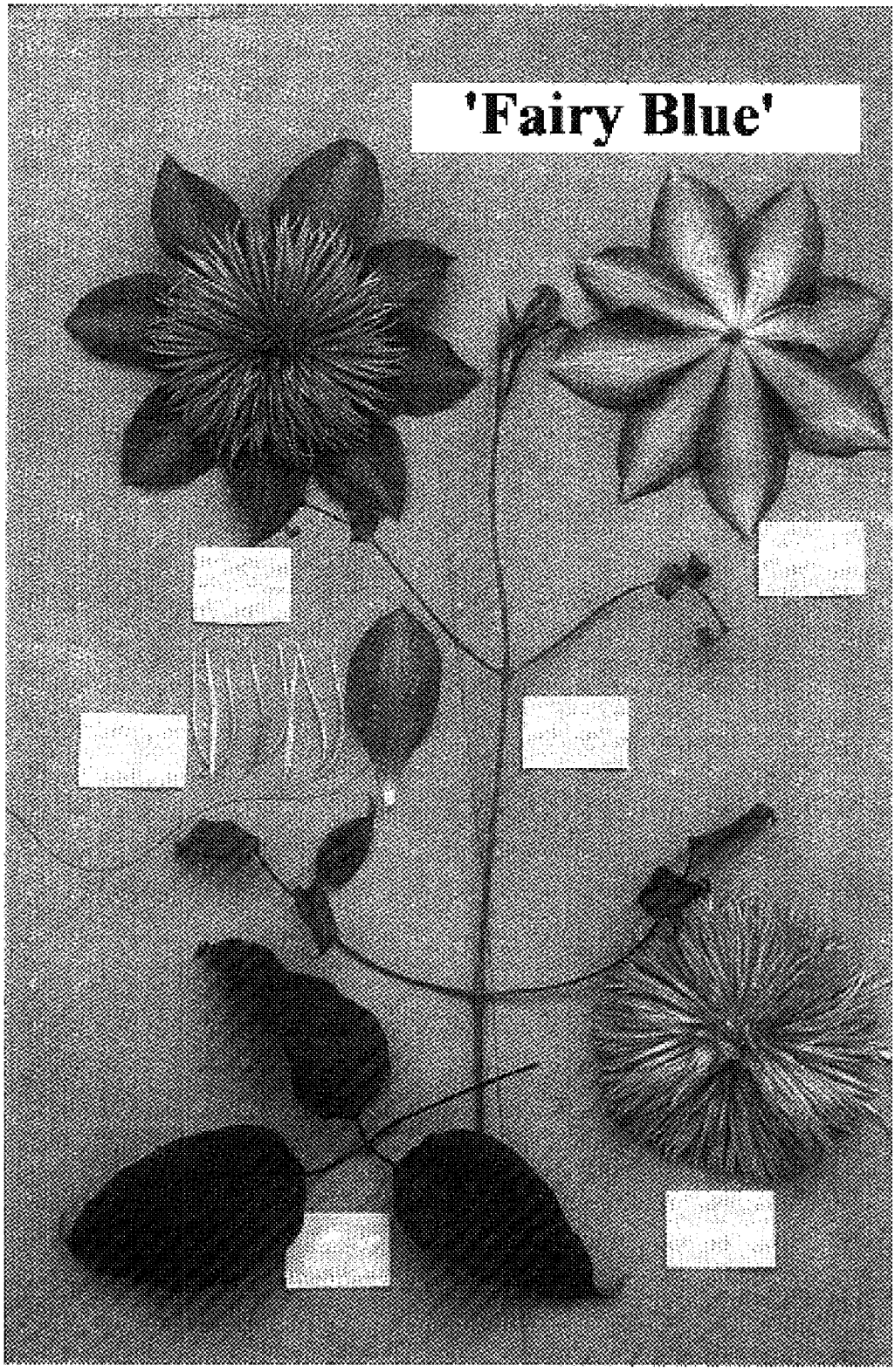
'Fairy Blue'